United States Patent

Chaudhuri et al.

[11] Patent Number: 5,427,773
[45] Date of Patent: Jun. 27, 1995

[54] QUATERNARY SALTS OF DIALKYLAMINOBENZAMIDES

[75] Inventors: Ratan K. Chaudhuri, Butler; Anatoly Alexander, Berkeley Heights; Anna A. Gripp, Whippany, all of N.J.

[73] Assignee: ISP Van Dyk Inc., Belleville, N.J.

[21] Appl. No.: 356,417

[22] Filed: Dec. 15, 1994

Related U.S. Application Data

[63] Continuation-in-part of Ser. No. 111,690, Aug. 25, 1993.

[51] Int. Cl.$^6$ .......................... A61K 7/06; A61K 7/42; C07C 229/00
[52] U.S. Cl. .......................... 424/60; 424/47; 424/70.9; 514/938; 562/450; 564/163
[58] Field of Search .............. 424/60, 70, 47; 514/938; 564/163; 562/450

[56] References Cited

U.S. PATENT DOCUMENTS

| | | | |
|---|---|---|---|
| 3,878,229 | 4/1975 | Strobel | 424/60 X |
| 3,879,443 | 4/1975 | Strobel | 424/60 X |
| 4,061,730 | 12/1977 | Kalopissis et al. | 424/59 |
| 4,069,309 | 1/1978 | Ciaudelli et al. | 424/60 X |
| 4,256,664 | 3/1981 | Epstein et al. | 424/60 X |
| 4,680,144 | 7/1987 | Conner | 424/60 X |
| 5,078,990 | 1/1992 | Martin et al. | 424/70 |

OTHER PUBLICATIONS

The Merck Index, 10th Ed., (1983), p. 1116, item 2658.
Steen, et al., C.A., 118: 51841 (1992).
Kimura, et al., C.A., 109: 31538 (1988).
Schanker, et al., C.A., 104: 61509 (1986).
Eaton, et al., C.A., 89: 208889 (1978).

*Primary Examiner*—Joseph Paul Brust
*Attorney, Agent, or Firm*—Marilyn J. Maue; Joshua J. Ward

[57] ABSTRACT

This invention relates to non-hydrolyzable, non-irritating, hair, skin and textile substantive quaternary salts of p-dialkylaminobenzamides having the formula

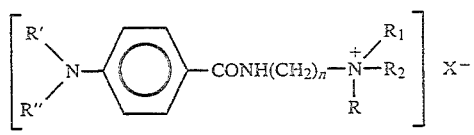

wherein R' and R'' are each selected from the group of $C_1$ to $C_2$ alkyl; n is an integer having a value of from 2 to 3; R is an alkyl radical having from 10 to 18 carbon atoms; $R_1$ and $R_2$ are each selected from the group of $C_1$ to $C_2$ alkyl, and X is an anion. These benzamide derivatives are active sunscreening agents which are usefully employed at a concentration of from about 0.5 to about 10 wt. % in a formulation requiring protection against the harmful effects of sunlight, such as skin burn, hair damage, color fading, etc.

35 Claims, No Drawings

QUATERNARY SALTS OF DIALKYLAMINOBENZAMIDES

This application is a continuation-in-part of Ser. No. 08/111,690, filed Aug. 25, 1993.

In one aspect the present invention relates to novel substantive compounds for skin, hair, paints, textiles and fibers of wool, cotton, silk and synthetics which provide protection from the undesirable affects of sunlight. In another aspect the invention relates to the use of such compounds as sunscreens in personal care or in other formulations.

BACKGROUND OF THE INVENTION

In addition to the recognized detrimental affects of sunlight on printed or colored fabrics and painted surfaces, human hair damage caused by sunlight in the ultraviolet spectrum is more severe than that resulting from all other factors such as weather, wind, atmospheric pollution, salt water, chlorinated water, perming, coloring, bleaching and improperly applied or repetitive treatments. Notwithstanding the need for effective sunscreens, none have been developed which provide desired hair substantivity while avoiding other deleterious changes in structure, brittleness, hair softness and the like. Prior attempts to remedy these problems have proven unsatisfactory. For example, U.S. Pat. Nos. 3,879,443; 3,878,229; 4,069,309 and 4,680,144 disclose various sunscreens dependent on an ester functionality. However, these compounds tend to be hydrolytically unstable to the extent that the formulator must avoid conditions conducive to hydrolysis during formulation. Also, since these esters lack hydrogen bonding capability with skin protein or hair keratin, their hair substantivity are not satisfactory.

U.S. Pat. No. 4,256,664 pertains to quaternized salicylamides; however, these compounds have poor dispersibility and have shown skin irritation. Further, the primary amines of this patent oxidize rapidly in air, thereby altering desired hair color and, in some instances, form nitroso amines some of which are known carcinogens. Finally, these amine compounds are subject to intermolecular and solvent hydrogen bonding which characteristic causes a significant shift in UV maxima absorption and reduces absorption in the desired spectrum range.

M. F. Saettone et al. in THE INTERNATIONAL JOURNAL OF COSMETIC SCIENCE, Vol. 8, 9-25, 1986, describes types of amido quaternaries based on salicyclic and cinnamic acids. The salicylamides are ortho substituted with spatial arrangements permitting internal molecular hydrogen bonding. The ortho relationship of the phenolic group to the bulky amide group causes steric hindrance and stress within the molecule. To counter this steric effect, the groups which deviate slightly from planarity are present. However, any minor deviation from planarity causes a reduction in the extinction coefficient and hence a corresponding reduction in the efficacy of protection against harmful sun rays. On the other hand, cinnamoylamides have additional unsaturation and conjugation with respect to both the aromatic ring and the carbonyl group. This structure permits electron delocalization to take place within the molecule; but, although the energy corresponding to this electron transition corresponds to a desired wavelength of about 305 nm, the molar extinction coefficient is materially lower than that for the corresponding para-dimethylamino carbonyl analog. Finally, the cinnamoyl compounds are subject to cis-trans isomerization as well as to oxidative cleavage and polymerization, i.e. characteristics to be avoided for effective sunscreens.

Still another patent, U.S. Pat. No. 4,061,730, seeks to remedy the above problems by the use of quaternized benzylidene camphor sunscreens. However, since quaternization eliminates conjugation in the compound, the sun protection efficiency is significantly reduced.

From the above discussion, it will be appreciated that the discovery of a commercially viable and hair substantive sunscreen is remote.

Accordingly, it is an object of the present invention to provide an effective, non-irritating sunscreening agent which is not subject to hydrolysis, and which has high substrate substantivity Another object of the invention resides in the synthesis of said sunscreening agent.

Still another object is to provide a novel water insoluble sunscreening agent for extended use in hair care.

These and other objects will become apparent from the following description and disclosure.

THE INVENTION

In accordance with the present invention, a substantially water insoluble, non-irritating and hydrolysis resistant cationic sunscreening agent is provided which possesses high molecular planarity and which is easily incorporated into commercial formulations to provide stable compositions.

The present benzamide derivatives can be employed to prevent color alteration in paints or painted substrates, e.g. automotive vehicles and mono or multi colored textile fabrics, and the like. Because of their high hair, skin and wool substantivity, the present compounds are particularly useful in cosmetic applications, as in hair conditioning shampoos, silicone containing softeners, hair conditioners and rinses, styling mousses, gels or lotions, hair sprays, hair dyes and bleaching compositions. Since the present compounds interact with hair protein, they provide UV protection and conditioning properties long after hair treatment. Beneficial cosmetic applications also include their compatability with and easy incorporation into skin care compositions, such as sun protection creams and lotions to inhibit skin ageing, wrinkle formation, erythema and carcinogenesis as well as in nail polish, lipstick, rouge or make-up bases. The benzamide derivatives of this invention also reduce fading of natural and synthetic dyes and minimize or eliminate photodegradation in dyed and undyed cotton, linen, silk and wool fabrics as well as color alteration in paints and painted surfaces exposed to climatic conditions as in automotive and house paints.

The non-hydrolyzable, non-irritating, substantive derivatives of this invention are quaternary ammonium salts of a para-dialkylamino aminobenzamide compound having the formula

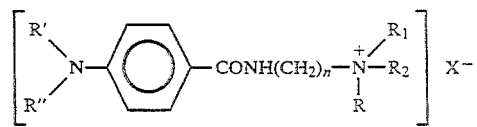

wherein R' and R" are each selected from the group of $C_1$ to $C_2$ alkyl; n is an integer having a value of from 2 to 4; R is a linear, branched or cyclic alkyl radical having from 10 to 18 carbon atoms and $R_1$ and $R_2$ are each selected from the group of $C_1$ to $C_2$ alkyl. It is to be understood that mixtures of the present benzamides can be employed in a composition to provide combined UV protection.

Of the above benzamide compounds, most preferred are those wherein R is alkyl having 12 carbon atoms and R', R", $R_1$ and $R_2$ are each methyl.

The present compounds are unique in that they absorb UV in wavelengths of from about 280 to about 330 nm and possess a molecular extinction coefficient of up to about 30,000. The present compounds are generally compatible with any composition requiring UV protection and can be added in an effective amount of between about 0.5 and about 10 wt. %, preferably between about 1 and about 3 wt. %, based on total composition.

Solutions of the present compounds are also usefully applied as a separate coating over a treated substrate. For example, a vehicle or aircraft can be sprayed or brushed, with a 2 to 10% solution of the present compound dissolved in a suitable solvent such as fatty alcohols, e.g. octyldodecanol, isocetyl alcohol, alkyl lactates containing 12 to 18 carbon atoms, 2-ethylhexyl p-dimethylamino benzoate (Padimate O), etc. The compound can also be pressed into a cosmetic cake as in a cake powder for application to the skin.

The benzamides of the present invention are easily synthesized according to the following two-stage reaction

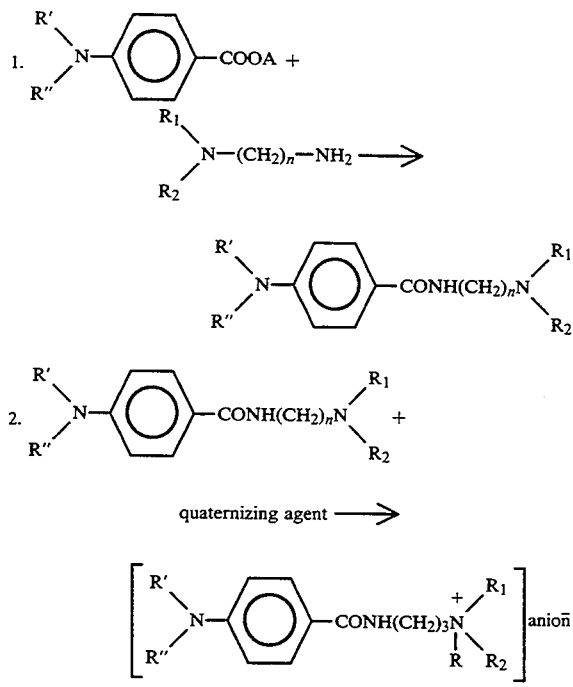

wherein A is $C_1$ to $C_8$ alkyl and the quaternizing agent is halogen, an anion forming organic moiety, e.g. alkyl tosylate, alkyl sulfonate, etc.

Stage 1 of the reaction is carried out at a temperature of between about 90° and about 180° C., preferably under reflux conditions for continuous removal of the alkanol by-product. The reaction of the aminobenzoate with diamine is conducted in the presence of a base catalyst such as dimethyl formamide, triethanol amine, N-methyl-morpholine, hexamethylene tetraamine, dimethylamino-2-hydroxy propane, 2,4,6-tris(dimethylaminomethyl)phenol, potassium t-butoxide, KOH, NaOH, $NaOCH_3$, $NaOC_2H_5$ and the like. Between about 0.5 and about 24 hours, in the presence of from about 0.1 to about 2 weight % of the base catalyst, is sufficient to complete the reaction to the aminobenzamide product in a high yield greater than 96%. Preferred conditions for this stage of the reaction include a temperature of from about 120° to about 170° C. for a period of between about 1 and about 5 hours. The aminobenzoate and diamine can be reacted as a melt or in a 15–50%, preferably a 20–30%, solids solution or emulsion in a suitable liquid medium provided by, e.g. acetone, methyl ethyl ketone, ethyl acetate, cyclohexane, octane, xylene, toluene, etc. and mixtures thereof. Also, the reaction can be effected under a pressure sufficient to maintain a liquid phase when needed.

The quaternization stage is carried out at a temperature of between about 70° and about 140° C., preferably between 100° and 130° C., and is completed within a period of from about 10 minutes to about 24 hours, more often 1 to 6 hours, after which the product can be recovered by crystallization, from ethyl acetate or a similar solvent. Although the product can be recovered in crystalline form, these crystals may contain up to 10 wt. % water, more desirably between about 1 and about 8 wt. % water.

The quaternizing agents employed in the present invention include $C_{10}$ to $C_{18}$ alkyl- halide, sulfate, sulfonate, acetal and aryl sulfonates, e.g. p-tolyl sulfonate. The alkyl moiety of the quaternizing agent can be branched or linear. Preferred quaternizing agents are those containing from 12 to 14 carbon atoms in the alkyl moiety.

In the above reactions, equimolar amounts of the reacting species are preferred; however, ratios of from about 1:2 to about 2:1 may be employed in the second stage reaction.

Advantages of the present sunscreening agents are derived from the aromatic $—N(R)_2$ group, which unlike $HO—C_6H_4—$ or $—NH_2$, is stable, is not sensitive to pH changes present in various formulations, and is not oxidized in air. The substitution of $—N(R)_2$ in the para-position on the phenyl ring also eliminates H bonding with protic solvents which characterize the ortho —OH and $—NH_2$ phenyl substitutions of other sunscreens while the replacement of the ester linkage found in prior compounds with an amide linkage provides an additional binding site for the hair protein (keratin) through H-bonding. The presence of the quaternary amine group provides the salt linkage through the electrovalent union of the side chain acid keratin residues thereby imparting conditioning properties. All of the above factors in combination provide the synergistic effects and benefits of the present sunscreens.

Formulations containing the present quaternized amino-benzamide compounds can be used in pump or aerosol sprays.

The cosmetic formulations incorporating the present sunscreens generally include between about 40 and about 90 wt. % of a carrier or propellant such as deionized water, alcohol, isobutane or propane, etc., between about 10 and about 40 wt. % of a surfactant or surfactant mixture such as sodium and/or ammonium, lauryl sulfate, sodium laureth sulfate etc., and fragrance and/or coloring agent as desired.

These formulations may optionally contain between about 5 and about 50 % of one or more inert components including a film forming polymer such as a $C_1$ to $C_4$ ester of a methyl vinyl ether/maleic anhydride copolymer, a vinyl pyrrolidone/vinyl acetate copolymer, etc.; a preservative such as bronopol, an ester of p-hydroxybenzoic acid, 2-methyl-3(2H) isothiazolone, a mixture of methyl and propyl paraben, dimethyl-5,5-dimethylhydantoin, Germall® 115, imidazolidinyl urea, etc.; a sequestrant, and an antistatic agent.

Following compilation of formulations serves to illustrate the diversity of formula types currently available in the marketplace. In each of the formulations the sunscreen of the present invention is employed.

| Ingredients | % w/w |
|---|---|
| A. Formula type: FACE CREAM | |
| Phase A | |
| Benzophenone-3 | 8.0 |
| Sunscreen | 6.0 |
| Cyclomethicone | 10.0 |
| Glyceryl stearate SE | 5.0 |
| Phenyldimethicone | 2.0 |
| Cetearyl alcohol (and) ceteareth-20 | 2.0 |
| Cetyl alcohol | 1.0 |
| Octyl palmitate | 10.0 |
| Phase B | |
| Water | QS |
| Preservative | QS |
| Glycerine | 5.0 |
| Diethanolamine p-methoxycinnamate | 8.0 |
| Titanium dioxide | 3.0 |
| Xanthan | 0.2 |
| Hydroxyethylcellulose | 0.1 |
| Phase C | |
| Fragrance | 0.3 |
| B. Formula type: w/o WATER-RESISTANT CREAM | |
| Phase A | |
| Mineral oil (and) lanolin alcohol | 5.0 |
| Isopropyl palmitate | 10.0 |
| Beeswax | 8.0 |
| Sorbitan sesquioleate | 2.0 |
| Mineral oil | 25.0 |
| Sunscreen | 6.0 |
| Benzophenone-3 | 4.0 |
| Phase B | |
| Water | QS |
| Borax | 0.4 |
| Preservative | QS |
| Propylene glycol | 5.0 |
| Phase C | |
| Fragrance | 0.25 |

| Ingredient | % w/w |
|---|---|
| C. Formula type: SUN BLOCK CREAM | |
| Phase A | |
| Isopropyl myristate | 9.0 |
| Sunscreen | 10.0 |
| Benzophenone-3 | 5.0 |
| Menthyl anthranilate | 5.0 |
| Stearic acid XXX | 5.0 |
| Glyceryl monostearate | 6.0 |
| Cetyl alcohol | 5.0 |
| PEG-40 stearate | 2.0 |
| Phase B | |
| Water | QS |
| Xanthan | 0.3 |
| DEA-cetyl phosphate | 8.0 |
| Preservative | QS |
| Glycerine | 3.5 |
| Phase C | |
| Fragrance | 0.25 |

-continued

| | |
|---|---|
| D. Formula type: WATER-PROOF LOTION | |
| Expected SPF: 15 | |
| Phase A | |
| Sunscreen | 8.0 |
| Benzophenone-3 | 4.0 |
| Myristyl myristate | 1.0 |
| Propylene glycol dipelargonate | 5.0 |
| Steareth-20 | 1.0 |
| Phase B | |
| Water | QS |
| Carbomer 1342 | 0.2 |
| Preservative | QS |
| Propylene glycol | 5.0 |
| Phase C | |
| PEG-15 cocamine | 0.2 |
| Phase D | |
| Fragrance | 0.25 |
| E. Formula type: CATIONIC SUNSCREEN LOTION | |
| Phase A | |
| Glycol stearate | 5.0 |
| $C_{12-15}$ alcohols benzoate | 3.5 |
| Sunscreen | 5.0 |
| PEG-40 stearate | 1.5 |
| Phase B | |
| Water | QS |
| Preservative | QS |
| Stearamidopropyl PG-dimonium chloride Phosphate | 3.5 |
| Glycerine | 4.0 |
| Phase C | |
| Fragrance | 0.3 |
| F. Formula type: GREASELESS SUNSCREEN OIL | |
| Benzophenone-3 | 3.0 |
| Sunscreen | 7.0 |
| Mineral Oil | QS |
| Octyl palmitate | 15.0 |
| Fragrance | 0.3 |
| Sesame Oil | 1.0 |
| BHA | 0.1 |
| G. Formula type: SUNSCREEN OIL | |
| Comments: Octyl palmitate reduces oiliness of mineral oil while minimizing UV curve shift | |
| Expected SPF: 3 | |
| Sunscreen | 4.0 |
| Octyl palmitate | QS |
| Lauryl lactate | 15.0 |
| Mineral oil | 35.0 |
| Isocetyl alcohol | 10.0 |
| Fragrance | 1.0 |
| H. Formula type: LIP BALM STICK | |
| Sunscreen | 7.0 |
| Benzophenone-3 | 3.0 |
| Castor oil | QS |
| Octyldodecanol | 5.0 |
| Beeswax | 15.0 |
| Ozokerite | 6.0 |
| Myristyl lactate | 4.0 |
| Candililla wax | 6.0 |
| Petrolatum | 5.0 |
| Fragrance | 0.5 |
| I. Formula type: Water-resistant sunscreen mousse | |
| Phase A | |
| Dimethicone | 10.0 |
| Sunscreen | 3.5 |
| Benzophenone-3 | 3.0 |
| Glyceryl PABA | 3.0 |
| Stearic acid XXX | 4.0 |
| Cetyl alcohol | 0.5 |
| Vitamin E acetate | 0.1 |
| Phase B | |
| Water | QS |
| Hydroxypropyl cellulose | 0.5 |
| Triethanolamine 99% | 0.5 |
| Ethanol | 20.0 |
| Preservative | QS |
| J. Formula type: Sunscreen mousse | |

-continued

| | |
|---|---|
| Water | QS |
| Propylene glycol | 5.0 |
| Quaternium-26 | 3.0 |
| Octyl methoxy cinnamate | 3.0 |
| Cetearyl alcohol (and) ceteareth-20 | 1.0 |
| Octyldodecanol | 5.0 |
| Preservative | QS |

K. Formula type: MAKE-UP MOUSSE

Phase A

| | |
|---|---|
| Glyceryl dilaurate | 2.5 |
| Glyceryl stearate SE | 3.0 |
| Cetyl alcohol | 1.5 |
| Decyl oleate | 2.5 |
| Propylene glycol depelargonate | 3.0 |
| Sunscreen | 3.5 |

Phase B

| | |
|---|---|
| Water | QS |
| Hydroxyethylcellulose | 0.5 |
| Sorbitol 70% | 5.0 |
| Pigment | 15.0 |
| Preservative | QS |

Phase C

| | |
|---|---|
| Ethanol | 20.0 |

L. Formula type: SUNSCREEN GELEE

| | |
|---|---|
| Myristyl lactate | 5.0 |
| Tridecylneopentanoate | 10.0 |
| Sunscreen | 4.0 |
| Petrolatum | QS |
| Paraffin | 5.0 |
| Beeswax | 4.0 |
| Calcium stearate | 5.0 |
| Cetearyl alcohol | 2.0 |
| Fragrance | 1.0 |
| Preservative | QS |

M. Shampoo

| | Parts |
|---|---|
| Emersol 6400 (sodium lauryl sulfate) | 30.0 |
| Rewomid DC-212/S (Cocamide DEA) | 5.0 |
| Deionized water | 60 |
| Preservative | QS |
| Sunscreen | 4 |

Preparation: Heat all ingredients to 45-50° C.; cool to room temperature

N. Hair Conditioner

| | |
|---|---|
| A. Sunscreen | 2.0% |
| Cetyl Alcohol | 2.0% |
| Ethoxylated Sorbitan Esters | 4.0% |
| B. Water | 92.0% |

Preparation: Heat both phases to 80° C.; add A to B with stirring and continue for 1 hour. Cool to room temperature.

O. Conditioning Shampoo Formulation, taken from Example 7 of U.S. Pat. No. 5,078,990, which are incorporated herein as representative teachings of suitable formulations for addition of the present sunscreens.

| ITEM | COMPONENT | WT. % |
|---|---|---|
| 1 | ammonium lauryl sulfate | 6.0 |
| 2 | ammonium laureth sulfate (1 mole EO) | 9.45 |
| 3 | sodium lauryl sulfate | 4.5 |
| 4 | distearyl dimethyl ammonium chloride (AROSURF ®) | 0.3 |
| 5 | distearyl phthalamic acid | 3.5 |
| 6 | sodium hydroxide | 0.085 |
| 7 | FD&C Blue #1 | 0.00024 |
| 8 | D&C yellow #10 | 0.0012 |
| 9 | tetrasodium EDTA/water softener | 0.2 |
| 10 | fragrance | 0.5 |
| 11 | DMDM hydantoin (GLYDANT ®) preservative | 0.1 |
| 12 | methyl & methylchloro isothiazolinone-preservatives | 0.05 |
| 13 | 33% SE-30 polysiloxane gum/67% SF96-350 polysiloxane oil | 2.5 |
| 14 | sunscreen | 0.8 |
| 15 | soft water | QS to 100 |

Add items #1, #2, and #3 and begin heating batch to

-continued

180° F.–185° F.
At 180° F. add item #4 and allow to completely mix in.
Add items #5, allow to mix in.
Add item #6, #7, and #8.
Allow to mix for 30 minutes at 180° F.–185° F.
After this time, samples should be cooled with item #15.

The conditioning agent (item 13) and sunscreen (14) then are added and mixed at a temperature of at least 30° C. and preferably at 40° C. to 50° C. The composition at this point exhibits lower frequency stretching bands at the higher temperatures and the conditioning agent is easily dispersed or dissolved within the emulsion without separation.

| Components | wt. % |
|---|---|
| Automotive Acrylic Enamel | |
| TiO$_2$ base containing 60% pigment | 220 |
| Color tinting base | 40 |
| Acrylic polymer (with pendant —OH and —COOH groups) 55% solids | 350 |
| Butoxy methylol melamine-formaldehyde resin - 55% solids | 230 |
| Butyl alcohol | 37 |
| Toluene sulfonic acid 50% in xylene | 2.6 |
| Xylene | 75.0 |
| Sunscreen | 5.4 |
| Propylene glycol methyl ether acetate | 40.0 |
| | 100.00 |
| Total solids | 45 wt. % |
| Pigment solids | 25 wt. % |
| Crosslinker of polymer | 30% |
| White Aircraft TopCoat | |
| 1:1 Aliphatic isocyanate-polyester polyol resin | 20.0 |
| TiO$_2$ (R960 Exterior grade) | 16.0 |
| Urethane catalyst | 2.0 |
| Flow/leveling/flood and float additives | 2.0 |
| Sunscreen | 10.0 |
| Mixture of methyl ethyl ketone, methyl isobutyl ketone and methyl allyl ketone | 50.0 |

Having generally described the invention, reference is now had to the accompanying Examples which illustrate preferred embodiments but which are not to be construed as limiting to the scope of the invention as more broadly defined above and in the appended claims.

EXAMPLE 1

Preparation of N-(3-Dimethylaminopropyl)-p-dimethylamino benzamide

Ethyl-p-dimethylaminobenzoate (164.9 g, 0.85 mole), 3-dimethylaminopropylamine (95.9 g, 0.94 mole) and sodium methoxide (2.8 g, 0.054 mole) were introduced into a 4-neck, 500 ml glass reactor, equipped with stirrer, heater, nitrogen purge and deflegmator with a Dean-Stark device. The charged reactor was flushed with dry nitrogen for 15 minutes at ambient temperature and was then heated to 150° C. under vigorous stirring. After about 15 minutes accumulation of distillate, the reactor temperature was gradually increased to 170° C. in 5° increments over a period of 1 hour and was then maintained at 170° C. for an additional hour, whereupon a sample of the product, analyzed by glass chromatography (GC) indicated 99+% conversion of the ester.

The resulting mixture was then cooled to 95° C. and washed twice with 200 ml of hot water after which the aqueous phase was cooled to room temperature and precipitated crystals recovered by filtration. These crystals were then combined with the organic phase in the reactor.

A vacuum of about 10–20 mm Hg was then applied to the product in the reactor which was heated to 90°–95° C. for 30 minutes. The resulting distillate containing water and light products was discarded. The residue was cooled to room temperature and was identified by elemental analysis, $^1$H and $^{13}$NMR and FTIR spectra, as N-(3-dimethylamino- propyl)-p-dimethylaminobenzamide. The product yield was 205 g (96.9% of theoretical based on ethyl-p-dimethylamino-benzoate).

EXAMPLE 2

Preparation of Stearyl-[3- (p-dimethyaminobenzamido) ethyl]-Dimethylammonium p-toluenesulfonate N-(3-dimethylaminoethyl)-p-dimethylaminobenzamide (77 g, 0.31 mole) prepared as in Example 1, except that dimethylamino ethyl amine is substituted for dimethylamino propyl amine and 131.5 g of stearyl-p-toluenesulfonate (0.31 mole) was heated to 110° C. under a blanket of nitrogen with continuous stirring for 2 hours. The resulting melt was dissolved in 800 ml of hot ethylacetate and then crystallized by cooling to ambient temperature. The crystals were recovered by filtration, dried in air and then under vacuum at 50°°60° C. The resulting whitish crystals of stearyl-[3-(p-dimethylaminobenzamido)ethyl]dimethyl ammonium p-toluenesulfonate were found to have a melting point of 122°–125° C. and the yield 191.8 g, was 92% of theoretical. The structure and purity of the product were confirmed by elemental analysis, NMR, FTIR and UV spectra.

EXAMPLE 3

Preparation of Hexadecyl-[3-p-dimethylaminobenzamido)ethyl]-dimethylammonium p-toluenesulfonate The synthesis as described in Example 2 was repeated except that 122.8 g of hexadecyl-p-toluene sulfonate (0.31 mole) was used as the quaternizing agent. The quaternized product yield was 181.8 g (91% of theoretical).

EXAMPLE 4

Preparation of Dodecyl-[3-(p-dimethylaminobenzamido)propyl]-dimethylammonium p-toluenesulfonate The synthesis as described in Example 1 was repeated except that 105.4 g of dodecyl-p-toluene sulfonate (0.31 mole) was used as the quaternizing agent and the quaternized product was crystallized from 1000 ml of methylethylketone. The yield was 149.6 g (82% of theoretical).

EXAMPLE 5

Demonstration of Substantivity

In order to demonstrate the substantivity and effectiveness of the present compounds to human hair, the following tests were carried out on the compounds of Examples 2 and 4. These were compared with benzylidene camphor para-toluene sulfonate (A) and 4-[(2-oxo-3-bornylidene)methyl]-phenyldimethyldodecylammonium paratoluene sulfonate (b) as disclosed in U.S. Pat. No. 4,061,730 and octyl-para-dimethylamino benzoate (C).

The test samples were prepared with 1 gram of human hair in a solution of 0.01% in water or isopropanol-water and using 50 ml of total solution. After standing for 2 minutes the hair was removed from the solution.

The substantivity of a sunscreening agent is determined in mg. of sunscreen absorbed/gram of hair, by substracting the absorbance at the maximum peak between 300 and 320 nm before and after dipping the hair in the solution containing the sunscreen. The results are as shown in Table I.

TABLE I

| Compound | Amount (in mg) of Sunscreen Absorbed per gm of Hair | Percentage of Sunscreen Absorbed on Hair |
| --- | --- | --- |
| Comparative A | 0 | 0 |
| Comparative B | 0 | 0 |
| 2 | 4.1 | 41 |
| 4 | 6.2 | 62 |

Comparative A is methoxy cinnamate diethanol amine salt.
Comparative B is 2-hydroxy-4-methoxy benzophenone-5-sulfuric acid neutralized with NaOH.

EXAMPLE 6

Demonstration of Hair Fading Reduction/Elimination

In order to demonstrate the effectiveness of the present compounds in reducing or elimination of the fading of dyed human hair, the following tests were carried out. Compounds of Examples 2 and 4 were selected for this study and octyl-p-dimethylamino-benzoate (C) was used as a comparative sunscreen. The test samples were prepared with 1 gram of dyed human hair in a solution (50 ml) of 0.01% in water or isopropanol-water. After standing for 10 minutes the hair was removed from the solution, one half was air dried, and the other half was rinsed for 5 minutes in tap water and then dried. Untreated dyed human hair was used as a control.

All test samples were irradiated with a Hanovia Ultra Violet Lamp containing a Corex D filter. It was found that at 72 hours, significant fading in both the octyl-p-dimethylaminobenzoate and control samples occurred. No fading of hair in the samples containing the sunscreens of Examples 2 and 4 took place.

The rinsed samples containing 2 and 4 sunscreens also retained about 80% of their fade resistance.

EXAMPLE 7

Demonstration of Hair Protection Against Sun Damage

The purpose of this study was to assess the ability of the products of this invention (Examples 2 and 4) to reduce the amount of ultraviolet light-induced damage to the hair, as measured by the change in fluorescence of mercurochrome-dyed hair samples. For this study, the sunscreen compounds were each dissolved in lauryl lactate (Ceraphyl 31) at 1 and 2% (W/W) level concentration.

The procedure followed in this study involves forming a base stain solution 1% mercurochrome in 6M urea containing 0.5% of aqueous Triton X-100* (Q.S. to 100 ml).

Degreased hair swatches are taken from 10 female subjects, 7 of which are permed or colored hair and 3 of which are virgin hair. The hair is cut ¼" from the scalp and the proximal 3" used for study.

A first portion of the hair strands from each subject is dipped into the base stain solution to which the sunscreen solution has been added.

A second equal portion of the hair strands from each subject is dipped into the base stain solution without addition of the sunscreen solution and the first and second portions are irradiated. Finally, a third equal portion of the hair strands from each subject is untreated and used as an absolute control to determine the amount of fluorescence inherent in the hair.

Measurement of fluoroescence is carried out by mounting three hair strands of a given sample on a microscope slide cross section. A fluorescence microscope Zeiss 2FL fitted with a photomultiplier tube (PMT) EM1#9798E and a filter measures fluorescence of the strands under −600 volts supplied by a Harrison 6515A DC supplier.

The results of these tests are reported in the following Table II.

TABLE II

|  | Fluorescence Units (Average of 10 Sample Subjects) | % Decrease in Fluorescence and Control |
|---|---|---|
| Hair samples treated with Sunscreen of Example 2 (1% soln) | 16.22 | 55.61 |
| Hair samples treated with Sunscreen of Example 4 (1% soln) | 18.30 | 51.92 |
| Hair samples treated with Sunscreen of Example 2 (2% soln) | 12.10 | 68.71 |
| Hair samples treated with Sunscreen of Example 4 (2% soln) | 13.55 | 64.91 |
| Hair samples in Ceraphyl 31 solution irradiated without sunscreen | 44.89 | 30.46 |
| Hair samples irradiated in the absence of Ceraphyl 31 and/or sunscreen | 38.71 | 25.0 |

The following represent some other formulations using the sunscreen agents of this invention and illustrate their compatability with a variety of components conventionally employed in such compositions.

EXAMPLE 8

Formulation of Hair Styling Mousse with Sun Protection

| 1. | Water | 85.5% |
|---|---|---|
| 2. | Gafquat 755N | 2.0% |
| 3. | Ethoxylated Sorbitol Esters | 2.0% |
| 4. | Ethanol | 5.0% |
| 5. | Preservative | 1.0% |
| 6. | Sunscreen from Example 2 or 4 | 1.5% |
| 7. | Propellant | |
|  | Dimethyl Ether | 4.0% |
|  | n-Butane | 4.0% |

Ingredient 2 above was added to water and heated to 55° C. with constant agitation until homogeneous, after which ingredients 3, 4 and 6, which had been mixed in a separate vessel until clear, were added with stirring for 1 hour and cooled. The preservative was then added and the resulting mixture introduced into an aerosol can with propellant.

EXAMPLE 9

Conditioning Hair Styling Gel and Sunscreen

A. Crosslinked methyl vinyl ether/maleic anhydride copolymer (6.0 wt. %) was dispersed in 80.2 wt. % of distilled water by mixing for about 45 minutes at about 87° C. The dispersion was then cooled to 60° C. and 0.4 wt. % of sodium hydroxyethyl glycinate followed by 7 wt. of deionized water was added while cooling to room temperature.

Hair Fixative

B. A separate mixture of 1 wt. % polyvinylpyrrolidone in 7 wt. % deionized water was prepared at room temperature and a dispersion consisting of 1.0 wt. % compound of Example 4 and 10.0 wt. % of polyethoxylated sorbitan monolaurate (Tween 20) was added with mixing to the aqueous polyvinylpyrrolidone phase at 70° C. The resulting mixture was then added to the crosslinked copolymer phase at 70° C. and mixing was continued while cooling to 25° C.

This formulation possesses excellent hair holding power while providing protection against sun damage.

EXAMPLE 10

Hair Conditioner for Dyed Hair

A dispersion of modified hydroxyethyl cellulose (0.75 wt. %) in 88.03 wt. % deionized water, 1.0 wt. % polyethoxylated sorbitan monolaurate and 0.50 wt. % phenoxyethanol was prepared at 85° C. To this dispersion was gradually added, at about 90° C. a premixed solution of 0.25 wt. % methylparaben, 0.25 wt. % propylparaben in 3.72 wt. % water. After mixing to uniformity, 2.0 wt. % glycol stearate, 1.0 wt. % mink amidopropyl dimethyl-2-hydroxyethyl ammonium chloride, 0.25 wt. % cetyl alcohol, 1.0 wt. % stearyl alcohol, and 1.0 wt. % of the compound of Example 2 were added in the above order and mixed for 10 minutes and then homogenized for 10 minutes at between about 80°-90° C. The resulting uniform mixture was then cooled to room temperature. This conditioning lotion when applied to dyed hair provides protection against hair surface damage due to exposure to the sun.

The hair substantivity of 1 g water wetted swatches European hair were subjected to spectrophotometric analysis which involved wetting the hair with 1.43 g of a saturated solutions of sunscreening agents shown in the table following Example 11 in 1,800 ml distilled water which was mixed and protected against light for 12 hours. The hair swatches were soaked in the solution for 1 minute and then dried, after which 5 ml of the remaining solution was transferred to a 100 ml volumetric flask, and diluted to volume with isopropyl alcohol.

Another 5 ml of solution into which no hair was soaked was then similarly prepared by dilution to volume with isopropyl alcohol in a 100 ml flask. The spectrophotometer was then set up to read absorbance of each solution in the 200–400 nm range using isopropyl alcohol as a blank.

EXAMPLE 11

Substantivity to Hair

The effectiveness of a sunscreening agent is also determined by its substantivity to hair and bears a strong relation to hydrogen bonding, salt linkages, Van der Wall's forces as well as hydrophobic-hydrophilic balance of the molecule. The following substantivity data shows the superiority of the products obtained by present invention over the previously described art.

| COMPOUND | | SUBSTANTIVITY (mg. product/gm of hair) |
|---|---|---|
| Dodecyl[(p-dimethyl-aminobenzamido)propyl] dimethylammonium tosylate | Present compd | 6.6 |
| Octyldodecyl [(p-dimethylaminobenz-amido) propyl] dimethylammonium tosylate | Present compd | 4.4 |
| Lauryl 3-dimethyl-aminoethyl p-dimethyl-aminobenzoyl tosylate | U.S. Pat. No. 4,680,144 | 3.7 |
| Stearyl 3-dimethyl-aminoethyl p-dimethyl-aminobenzoyl tosylate | U.S. Pat. No. 4,680,144 | 2.6 |
| Lauryl 3-salicylamido propyl dimethyl ammonium bromide | U.S. Pat. No. 4,256,664 | 2.4 |
| Lauryl [(p-aminobenz-amido) propyl] dimethylammonium bromide | U.S. Pat. No. 4,256,664 | 2.2 |

EXAMPLE 12

Organic sunscreens are generally unsuitable for application to human hair because of inadequate substantivity as they tend to rinse-out of the hair and are accordingly ineffective. Previous attempts to remedy these shortcomings and have not proved effective for the following reasons:

Sunscreen Efficacy

The effectiveness of a sunscreening agent is determined by dividing the absorbance at the maximum peak between 300 and 320 nm by the concentration in grams per liter. This is known as the "K" value of a sunscreening agent. The higher the "K" value, the better the sunscreening ability and the lower the amount of material needed for protection from sun. In other words, from the "K" value the amount of sunscreening agent necessary for protection from the sun ultraviolet radiation can be determined and used in any cosmetically acceptable base preparation. The following data shows the superiority of the products obtained by present invention over related compounds.

| COMPOUND | | K VALUES |
|---|---|---|
| Dodecyl [(p-dimethylaminobenz amido)propyl] dimethylammonium tosylate | Present compd. | 47 |
| Octyldodecyl [(p-dimethylaminobenz amido)propyl] dimethylammonium tosylate | Present compd. | 41 |
| Lauryl 3-dimethylamino-ethyl p-dimethyl-aminobenzoyl tosylate | U.S. Pat. No. 4,680,144 | 44 |
| Stearyl 3-dimethylamino-ethyl p-dimethyl-aminobenzoyl tosylate | U.S. Pat. No. 4,680,144 | 37 |
| Lauryl 3-salicyl-amidopropyl dimethyl ammonium bromide | U.S. Pat. No. 4,256,664 | 19 |
| Lauryl [(p-amino-benzamido) propyl]dimethyl-ammonium bromide | U.S. Pat. No. 4,256,664 | 22 |

EXAMPLE 13

Hydrolytic Stability

The effectiveness of a sunscreening agent is also determined by its hydrolytic stability. We have found that the products developed in this inventive efforts are extremely stable in presence of fatty alcohols (common ingredients in hair conditioners) where as the products described in U.S. Pat. 4,680,144 are not. 10 to 25% product loss due to transesterification with fatty alcohols were observed when heated around 90 to 100° C. for 4 hours under acidic conditions pH 2 to 4).

The following is a summation showing the superiority of the present products over those described in related art.

| | p-Dimethylamino benzamides | p-Dimethylamino benzoates | Salicylamides | p-Aminobenzamides |
|---|---|---|---|---|
| U.S. Pat. No. | Present Invention | 4,680,144 and 3,878,229 | 4,256,664 | 4,256,664 |
| Molar Extinction[1] Coefficient | ~27,000 | ~27,000 | ~4,900 | ~15,300 |
| Hair Substantivity (mg/G of Hair) | 6.6[2] | 4.1 | 3.9 | 2.8 |
| Hydrolytic Stability | Very stable in both basic and acidic conditions | Not stable in basic conditions | Not stable in basic conditions | Not stable in acidic and basic conditions |
| Dispersibility[4] | Easily dispersible in formulation media | Less dispersible | Poor dispersibility | Poor dispersibility |
| Skin compatibility | Substantially Nonirritant[3] | Slightly irritant | Irritant | Irritant |
| Solvent Shift in UV maxima | None | None | Large Shift | Large Shift |

[1]Higher the value, the better the sunscreen protection ability and the lower the amount of material needed for protection.
[2]Improved substantivity comes from a combination of hydrogen bonding capability with hair protein and the products water solubility.
[3]Skin compatibility comes from a combination of resemblance of amide functionality with the peptide linkage of hair protein (Keratin) and the absence of primary amine or phenolic hydroxyl functionalities.
[4]Dispersibility of the product is key in determining how well the product is going to spread on the substrate.

EXAMPLE 14

Formulation of Hair Conditioner with Sun Protection

| A. | Sunscreen of Example 4 | 2.0% |
|---|---|---|
| | Cetyl Alcohol | 2.0% |
| | Ethoxylated Sorbitan Esters | 4.0% |
| | Dodecyl Pyrrolidone | 0.5% |

| -continued | |
|---|---|
| B. Water | 91.5% |

After adding phase A to B above, the resulting mixture was heated to 80° C., for 1 hour and then cooled to room temperature to produce a creme of relatively low viscosity. Shampooed hair treated with this product had a lustrous and silky appearance.

It will be understood that other formulations involving the compounds of this invention provide the benefits described herein and are within the scope of this invention.

What is claimed is:

1. The quaternary ammonium salt of a paradialkylamino benzamide having the formula

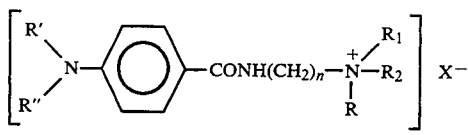

wherein R' and R" are each selected from the group of $C_1$ to $C_2$ alkyl; n is an integer having a value of from 2 to 3; R is an alkyl or carboxyalkyl radical having from 10 to 18 carbon atoms; $R_1$ and $R_2$ are each selected from the group of $C_1$ to $C_2$ alkyl and X is an anion.

2. The quaternary salt of claim 1 wherein R is alkyl having 12 to 18 carbon atoms.

3. The quaternary salt of claim 1 wherein said anion is selected from the group of chloride, bromide, alkyl sulfate, alkyl sulfonate and p-tolyl sulfonate.

4. The quaternary salt of claim 1 wherein said salt is in crystalline form and contains between about 1 and about 8 wt. % moisture.

5. The quaternary salt of claim 1 having the formula

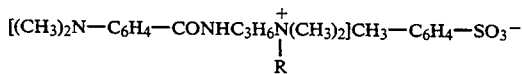

where R is alkyl having from 12 to 18 carbon atoms.

6. The quaternary salt of claim 1 which is stearyl-[3-(p-dimethylaminobenzamido)propyl]-dimethyl ammonium p-toluenesulfonate.

7. The quaternary salt of claim 1 which is dodecyl-[3-(p-dimethylaminobenzamido)ethyl]-dimethyl ammonium p-toluenesulfonate.

8. The quaternary salt of claim 1 which is dodecyl-[3-(p-dimethylaminobenzamido)propyl]-dimethyl ammonium p-toluenesulfonate.

9. The quaternary salt of claim 1 which is cetylstearyl-[3-(p-dimethylaminobenzamido)propyl]-dimethyl ammonium p-toluenesulfonate.

10. The quaternary salt of claim 1 which is stearyl-[3-(p-dimethy laminobenzamido)propyl]-dimethyl ammonium chloride.

11. The quaternary salt of claim 1 which is tetradecyl-[3-(p-dimethylaminobenzamido)propyl]dimethyl ammonium chloride.

12. A sunscreening composition containing a carrier and an effective sunscreening amount of a quaternary ammonium salt of a para-dialkylamino benzamide of claim 1.

13. The sunscreening composition of claim 12 wherein a mixture of said quaternary ammonium salts of para-dialkylamino benzamides are employed.

14. The sunscreening composition of claim 12 wherein said quaternary salts have the formula

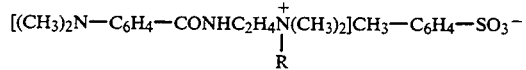

wherein R, in the mixture is alkyl having from 12 to 18 carbon atoms.

15. The sunscreening composition of claim 12 wherein said quaternary salts have the formula

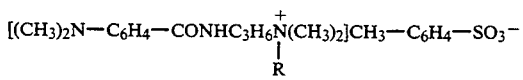

wherein R, in the mixture is alkyl having from 12 to 18 carbon atoms.

16. The composition of claim 12 wherein said sunscreen is stearyl-[3-(p-dimethylaminobenzamido) propyl]-dimethyl ammonium p-toluenesulfonate.

17. The composition of claim 12 wherein said sunscreen is dodecyl-[3-(p-dimethylaminobenzamido)ethyl]-dimethyl ammonium p-toluenesulfonate.

18. The composition of claim 12 wherein said sunscreen is cetylstearyl-[3-(p-dimethylaminobenzamido)-propyl]-dimethyl ammonium p-toluenesulfonate.

19. The composition of claim 12 wherein said sunscreen is stearyl-[3-(p-dimethylaminobenzamido) propyl]-dimethyl ammonium chloride.

20. The composition of claim 12 wherein said sunscreen is dodecyl-[3-(p-dimethylaminobenzamido) propyl]-pyrrolidinium bromide.

21. The composition of claim 12 wherein said sunscreen is dodecyl-[3-(p-dimethylaminobenzamido)ethyl]-pyrrolidinium bromide.

22. The sunscreening composition of claim 12 which additionally contains one or more of the components selected from the group of a surfactant, a neutralizer, a stabilizer, a propellant, a coloring agent, a fragrance, a film forming polymer, a preservative, an antistat and a sequestrant.

23. The composition of claim 12 which is in admixture with a standard hair or skin treating formulation.

24. The composition of claim 12 which is in admixture with a paint formulation.

25. The quaternary salt of claim 1 wherein R is alkyl having from 12 to 14 carbon atoms.

26. A sunscreening composition of claim 12 wherein said carrier is a hair rinse-off formulation.

27. A sunscreen composition of claim 12 wherein said carrier is a formulation which remains on the hair after shampooing.

28. A sunscreening composition of claim 12 wherein said carrier is a hair conditioner formulation.

29. A sunscreening composition of claim 12 wherein said carrier is a mousse formulation.

30. A sunscreening composition of claim 12 wherein said carrier is a shampoo formulation.

31. A sunscreening composition of claim 12 wherein said carrier is a hair spray formulation.

32. A sunscreening composition of claim 12 wherein said carrier is a hair fixative formulation.

33. A sunscreening composition comprising a hair surface conditioning amount of the quaternary ammonium salt of claim 1 and a carrier therefor.

34. A sunscreening composition comprising a disulfide bond cleavage reducing amount of the quaternary ammonium salt of claim 1 and a carrier therefor.

35. A sunscreening composition comprising a tryptophane cleavage reducing amount of the quaternary ammonium salt of claim 1 and a carrier therefor.

* * * * *